United States Patent [19]

Grace et al.

[11] Patent Number: 4,919,508
[45] Date of Patent: Apr. 24, 1990

[54] FIBEROPTIC COUPLER

[75] Inventors: Kenneth P. Grace, Woodland Park; Facundo Aparicio, Colorado Springs, both of Colo.

[73] Assignee: The Spectranetics Corporation, Colorado Springs, Colo.

[21] Appl. No.: 228,278

[22] Filed: Aug. 4, 1988

[51] Int. Cl.[5] .............................................. G02B 6/42
[52] U.S. Cl. ............................... 350/96.20; 350/96.26
[58] Field of Search .............. 350/96.20, 96.21, 96.22, 350/96.25, 96.26; 128/303.1

[56] References Cited

U.S. PATENT DOCUMENTS

| 2,517,689 | 7/1947 | Lement . | |
|---|---|---|---|
| 3,032,359 | 5/1958 | Cator . | |
| 3,196,897 | 10/1962 | Hodson . | |
| 3,430,990 | 11/1966 | Nelson . | |
| 3,649,053 | 3/1972 | Snyder | 285/110 |
| 3,695,642 | 10/1972 | DeWoody | 285/133 R |
| 3,761,197 | 9/1973 | Shendure | 285/277 |
| 3,820,827 | 6/1974 | Boelkins | 285/133 R |
| 3,897,089 | 7/1975 | Leichsenring et al. | 285/185 |
| 4,031,358 | 6/1977 | Thorniley | 350/96.26 X |
| 4,114,853 | 9/1978 | Medvick | 251/149 |
| 4,423,922 | 1/1984 | Porter | 350/96.15 |
| 4,435,036 | 3/1984 | Sasakawa | 350/96.20 |
| 4,593,970 | 6/1986 | Rhodes | 350/96.20 |
| 4,607,911 | 8/1986 | Rhodes | 350/96.20 |
| 4,760,845 | 8/1988 | Kovalcheck | 128/303.1 |

Primary Examiner—John D. Lee
Assistant Examiner—Phan T. Heartney
Attorney, Agent, or Firm—Cushman, Darby & Cushman

[57] ABSTRACT

A coupler for efficiently coupling a laser light source to a fiberoptic catheter. The coupler contains coding for determining information about the catheter, such as the size of the optical fiber catheter which it is coupling.

11 Claims, 6 Drawing Sheets

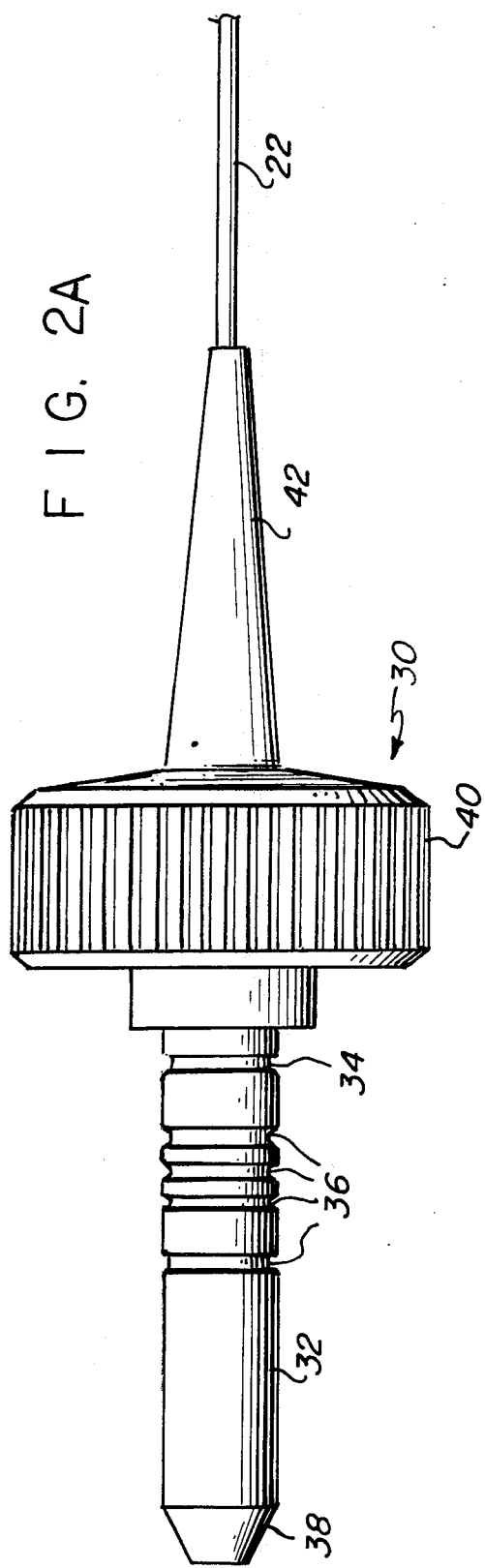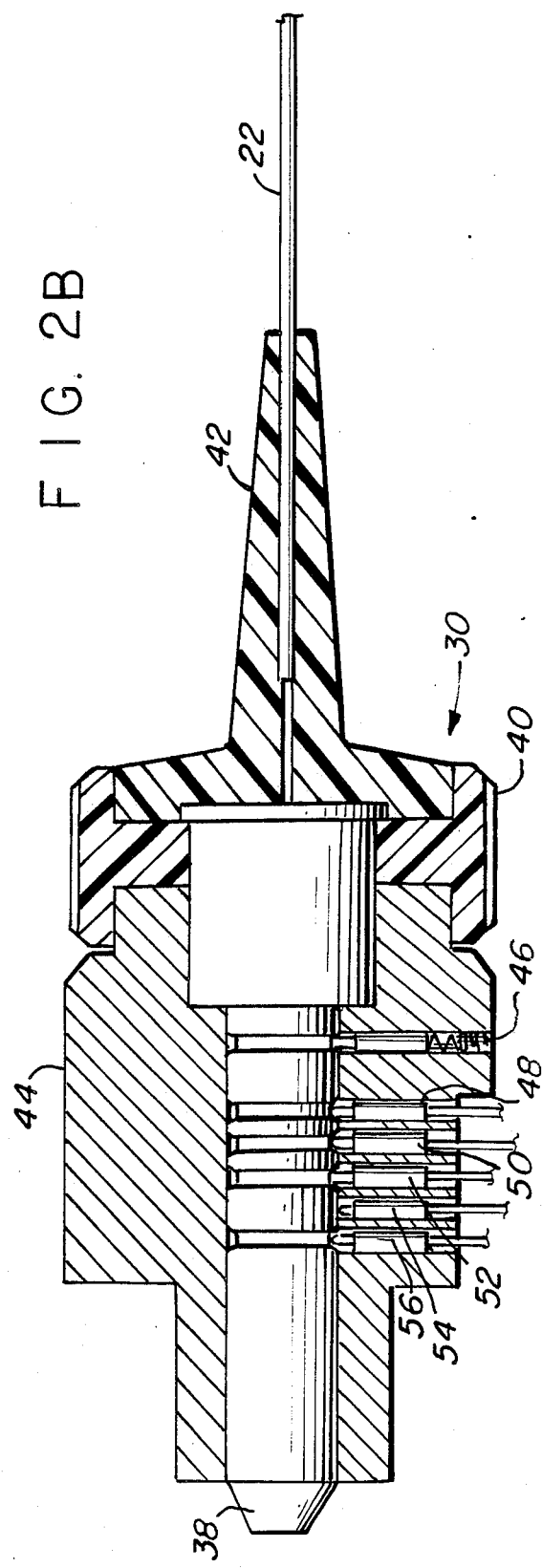

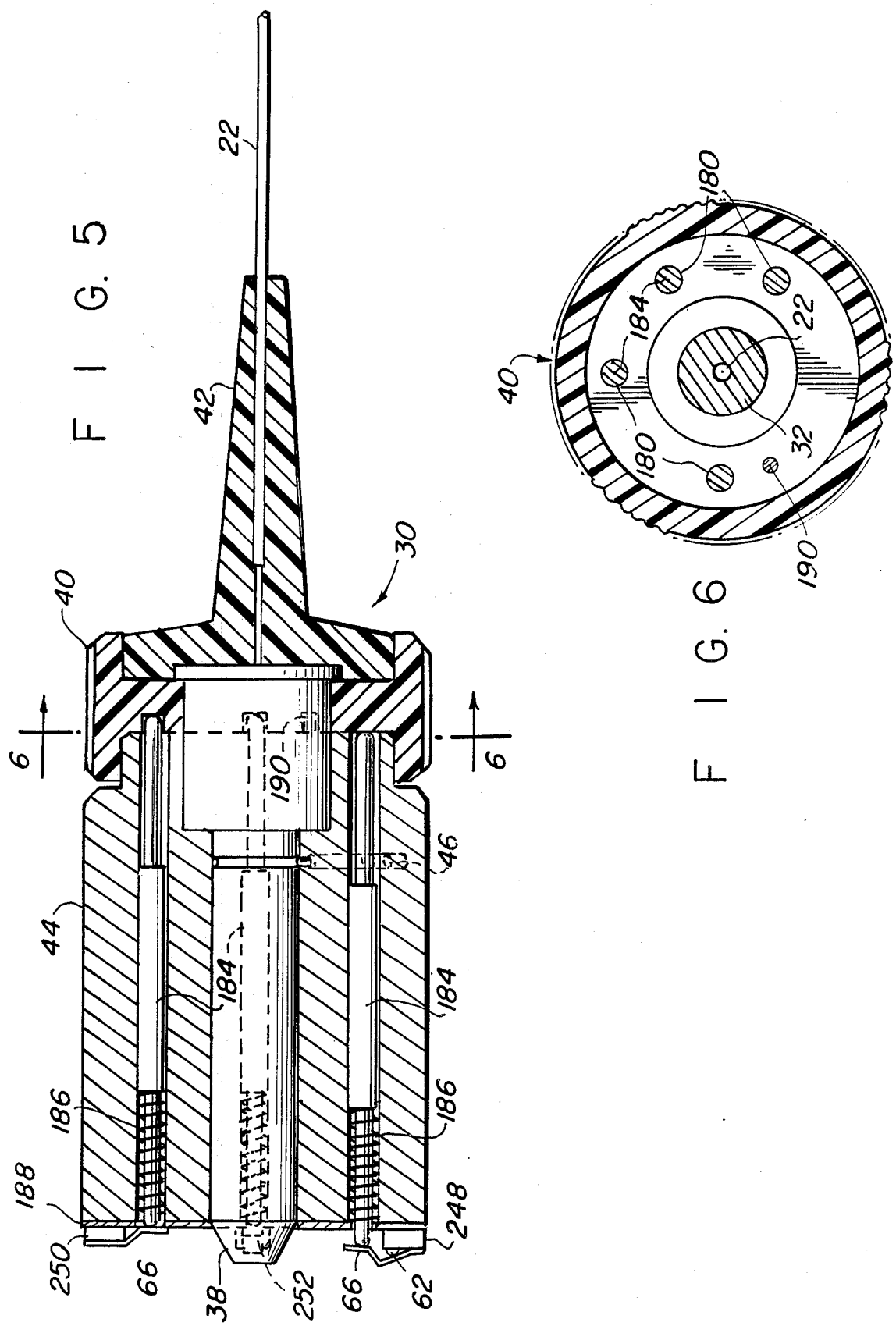

FIBEROPTIC COUPLER

BACKGROUND OF THE INVENTION

The invention relates to an apparatus for coupling an optical fiber to a laser light source. More particularly, this invention relates to a quick disconnect coupler which can mate optical fibers of varying size to a laser light source, the coupler of this invention being able to detect information concerning a characteristic such as size, of the optical fiber being mated to the laser light source.

In the field of medicine, it is desirable to insert optical fiber catheters into the human body to probe and inspect various portions of the body. One such technique is to surgically insert a catheter into a main blood vessel and pass the catheter to various organs, such as the heart, for inspection. A technique being used today is to insert an optical fiber catheter attached to a laser energy source into the body and then use laser pulses to destroy materials blocking blood vessels or remove any material towards which the optical fiber catheter directs the laser energy.

Obviously, each catheter can be employed with only one patient. Accordingly, the catheters are disposable. Since the size of the blood vessels in human bodies varies according to age and physical attributes, different size fiberoptic catheters are needed. Therefore, a quick connect/disconnect feature for attaching the fiberoptic catheter to a laser light source is needed.

The optical coupler for attaching an optical fiber catheter to a laser source must accurately align the optical fiber with the light source to permit near 100% coupling of the laser light into the optical fiber. This requires a particularly accurate coupler.

Various types of quick connect tubing couplers are known in the art. An example is U.S. Pat. No. 3,032,359 to Cator, May 1, 1962, which discloses a snap action coupler for tubing having a locking means to prevent leakage at the coupler. A more recent example is shown in U.S. Pat. No. 4,114,853 issued Sept. 19, 1978 to Medvick wherein a closely fitting male member provides a releasable coupling with a female member. The known tubing couplers are designed to provide a repeatable leak free seal between two tubes. No use with optical fibers is made or suggested.

Optical fiber couplers such as those disclosed in U.S. Pat. No. 4,435,036 to Sasakawa and U.S. Pat. No. 4,607,911 to Rhodes show the use of a two part connector, the two parts being coupled by threaded engagement. Neither coupler is of a quick disconnect design nor does the coupler provide any information about the optical fibers being coupled. Likewise, the directional coupler disclosed in U.S. Pat. No. 4,423,922 to Porter uses a threaded engagement of an optical fiber and does not provide any information about the fiber being coupled.

When employing fibers of varying size, it is important to know the size of the fiber being attached to the laser source. When employing lasers to vaporize or otherwise remove material, the energy density per laser beam pulse is critical. Too great an energy density may damage human tissue which was not to be removed or cause damage to the optical fiber. As the size of the fiber varies, the energy density per pulse will also vary. Therefore, in addition to accurately aligning and coupling an optical fiber catheter to a laser light source, the optical coupler should recognize the size of fiber catheter to which it is coupling so that the energy emitted by the laser can be controlled.

SUMMARY OF THE INVENTION

The present invention is a quick disconnect coupler for an optical fiber which accurately aligns the optical fiber to a laser light source and conveys information concerning a characteristic of the fiber, such as the size of the fiber which is being coupled. The coupler comprises a first connector portion having a locking grove which permits accurate alignment of the fiber to a second connector portion mounted on the laser light source.

A means for providing information indicative of the optical fiber is contained in the first connector portion. The second connector portion is removably connected to the first connector portion and contains means for decoding information about the fiber to which it is being coupled. Information may be coded in the first connector portion by a series of grooves whose position and number provide information as to its optical fiber size. A series of sensors contained in the second connector portion of the coupler determines the coding of the grooves and provides information as to the size, e.g., diameter, of the fiber being coupled to the laser light source.

The coupler may have a male locating pin contained in the first connector portion and a cooperating female receptacle in the second connector portion. A series of grooves in the male locating pin may provide information which can be decoded by a series of microswitches in the female receptacle.

In an alternative embodiment, information may be coded in the first connector portion by a series of relief openings or slots whose presence and location are related to the optical fiber characteristics. A series of sensors contained in the second connector portion determines the coding of the relief openings and provides information as to the size, diameter, or other characteristics of the fiber catheter being coupled to the laser light source.

The preferred embodiment is described in relation to a fiber delivery system adapted to be inserted in a subject through a catheter. Of course, the present invention can be employed with other applications in which laser energy is directed along an optical fiber.

BRIEF DESCRIPTION OF THE DRAWINGS

FIG. 2a is a drawing of the male portion of the optical fiber catheter;

FIG. 2b is a cross-sectional view of the coupler in a mated position;

FIG. 5 is a cross-sectional view of an alternative embodiment of the coupler shown in a mated position;

FIG. 6 is a cross-sectional view of the male portion showing the relief openings;

DETAILED DESCRIPTION OF THE PREFERRED EMBODIMENT

Figure 1:
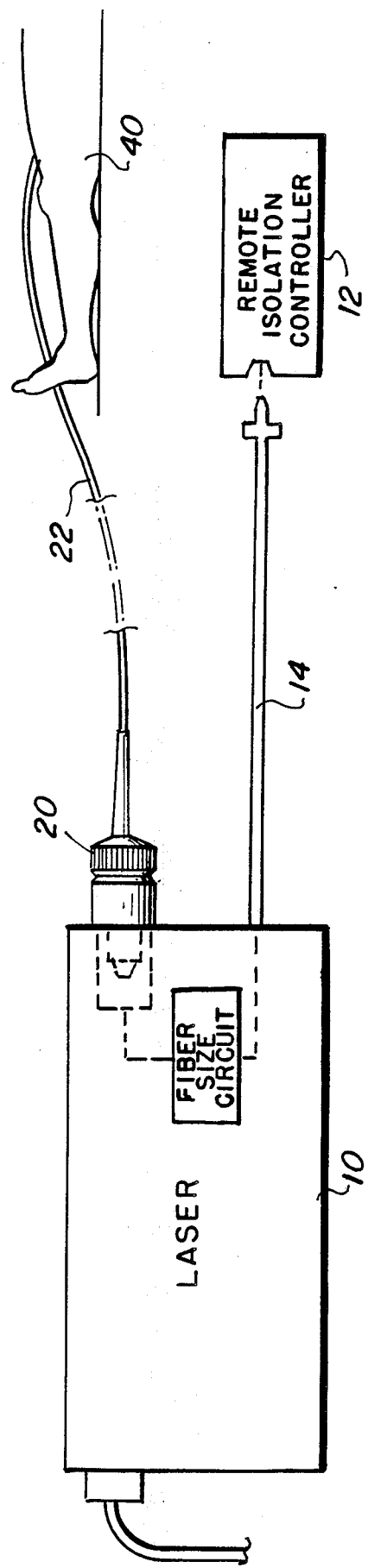
FIG. 1 is a diagram of the laser fiberoptic catheter system employing the coupler of the present invention.

Shown in FIG. 1 is a layout of the overall system employing the fiberoptic coupler of the present invention. A laser source 10 contains the power supplies and laser optics to output a laser light beam of a desired energy level. The laser is controlled by a remote isolation controller 12 which controls the intensity and duration of the laser pulse via an optically isolated cable 14. Optical coupler 20 of the present invention connects a fiberoptical catheter 22 to laser source 10. Fiberoptic catheter 22 can be surgically inserted into the groin or other area of a patient 40. Associated within laser source 10 is electronic circuit 60 used in conjunction with optical coupler 20 to determine the presence and size of fiberoptic catheter 22 which is connected to laser source 10.

Fiberoptic coupler 20 as shown in FIG. 2a comprises a male plug portion 30 having a locating pin 32 which is clad about or coupled to an end of fiberoptic catheter 22. Male plug 30 contains a locking groove 34 and fiber diameter indicating grooves 36. Tip 38 of locating pin 32 is tapered to allow easy insertion of the pin within the female receptacle portion of the optical coupler. Enlargement 40 of male plug portion 30 can be used as a handle and provides a means for grasping and inserting a disposable catheter into the female portion. Enlarged region 40 may be plastic and have a silicon rubber support 42 extending away from the handle towards fiberoptic catheter 22 to provide support for and smooth flexing of catheter 22.

A cross-sectional view of fiberoptic coupler 20 in a mated position is shown in FIG. 2b. Female receptacle portion 44 of optical coupler 20 is connected to receive energy from laser source 10. Locating pin 32 can be seated within metal female housing 44 which contains a spring loaded locking plunger 46 which presses against locking groove 34 to provide a rigid and accurate alignment of tip end 38 of male plug portion 30. This accurately aligns the optical fiber of catheter 22 to laser source 10. Also contained within housing 44 is a series of microswitches 48, 50, 52, 54 and 56 which sense the presence or absence of size indicating grooves 36 at corresponding locations along locating pin 32.

Figure 3:
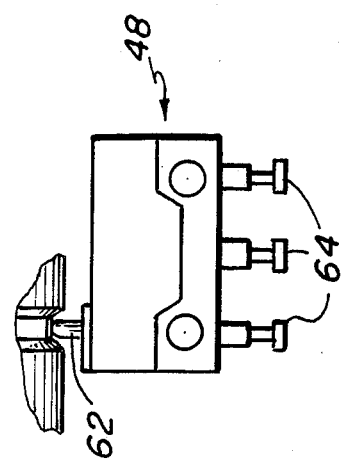
FIG. 3 is a detailed view of an electrical microswitch sensing a groove.

Microswitch 48 is shown in detail in FIG. 3 wherein an actuating member 62 causes contacts of switch 48 to be opened or closed depending upon whether a groove is located in a position to depress actuating member 62. Electrical connections are made to microswitch 48 via leads 64. The switch is of standard commercially available design and can be electrically connected to be either normally opened or normally closed.

Figure 4:
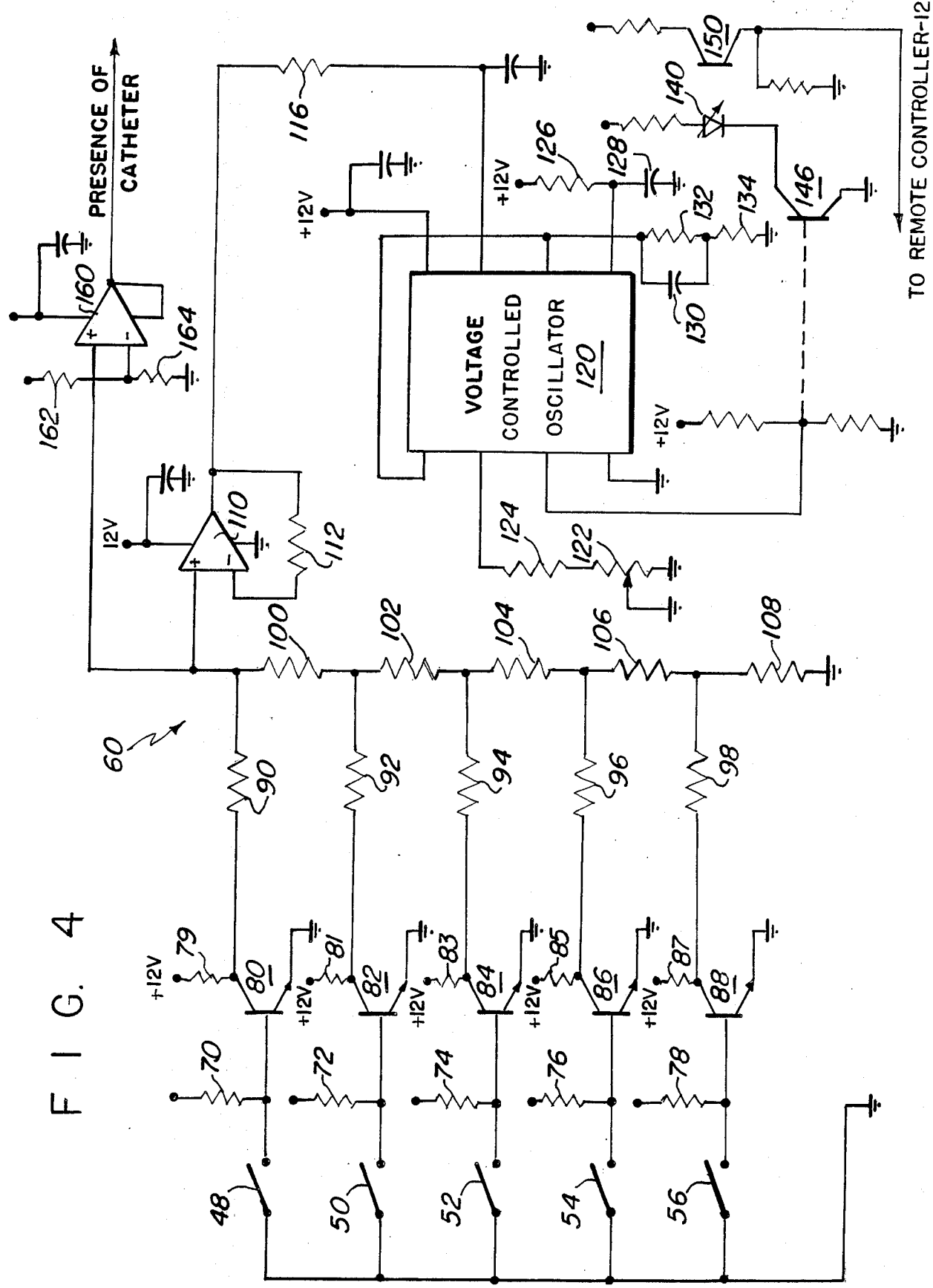
FIG. 4 is a schematic drawing of a circuit for determining the presence and size of a fiberoptic catheter.

The output of the switches is sensed by circuit 60 shown in detail in FIG. 4 wherein switches 48–56 are shown as making contact to ground when closed. Connected to each switch is a transistor network containing pull up resistors 70, 72, 74 76 and 78 connected to transistors 80, 82, 84, 86 and 88, respectively, as shown. Transistors 80–88 have load resistors 79, 81, 83, 85 and 87, respectively, connecting the transistors to a power supply. The emitter of each transistor is connected to ground. When one of microswitches is closed, the associated transistor has its base voltage grounded causing the voltage at the collector to rise to approximately the power supply voltage. The conduction states of transistors 80–88 cause currents to flow through resistors 90, 92, 94, 96 and 98 which, in turn, cause voltage drops across resistors 100, 102, 104, 106 and 108. Thus, a voltage is applied to operational amplifier 110. This voltage is uniquely related to which of switches 48–56 is closed. The voltage applied to amplifier 110 contains information concerning which combination of switches is closed. The gain of operational amplifier 110 is controlled, in part, by the value of resistor 112. The output of amplifier 110 is a DC analog voltage which is related to which of switches 48–56 are opened or closed. The analog output is applied through resistor 116 to a voltage controlled oscillator 120. Voltage controlled oscillator 120 can be fine-tuned by resistors 122, 124, 126, 132 and 134 and capacitors 128 and 130 to produce an AC output whose frequency is directly related to DC voltage input, and therefore, to which of switches 48–56 are closed. This AC output of voltage controlled oscillator 120 is through buffer transistor 146 with optical coupling provided by photodiode 140 and photo transistor 150 to remote controller 12 which uses the frequency of the signal to control the energy emitted per pulse by laser source 10.

Additionally, the output across the resistor network 100–108 is provided to one input of operational amplifier 160. Resistors 162 and 164 set a reference voltage at the other input of amplifier 160. With this arrangement, amplifier 110 acts as a comparator to provide an output which is indicative of the presence of any optical fiber and can be used to control the opening and closing of a shutter of laser source 10.

Any number of different circuit schemes can be devised to handle the output of the microswitches used in the electrical sensing of the optical fiber. The optical fiber coding of the male plug portion shown in FIG. 2b could be coded as 01000 and correspond to a logic state represented by a binary 8.

An alternate embodiment for encoding information about the optical fiber is shown in FIG. 5. The male plug portion 30 is shown with fiberoptic catheter 22 connected to enlarged handle region 40 and having a support 42 of silicon rubber or other material. Enlarged handle region 40 contains a number of relief slots 180 whose presence or absence is indicative of the characteristics of the fiberoptic catheter 22.

Female housing 44 contains a series of plungers 184 in longitudinal bores of the female housing 44. Plungers 184 are urged upward by springs 186 which push against the plunger 184 and spring keeper cover 188. Plungers 184 are narrowed at its one end to fit into relief slot 180, if present. At the end of plunger 184, away from male portion 30, the plunger activates a microswitch 248 having an actuating member 62 which is triggered through a lever arm 66.

To ensure proper angular orientation between female housing 44 and male plug portion 30, a pin 190 is placed in housing 44 to rotationally align and hold housing 44 and plug 30 in a fixed position.

As can be seen in FIG. 5, one plunger 184 is seated in relief slot 180 causing microswitch 250 to close while another plunger has failed to find a relief slot 180 and causes the microswitch 248 to remain open.

A cross-sectional view of FIG. 5 taken through the enlarged handle region 40 showing the junction of the female housing 44 and male plug 30 is shown in FIG. 6. Relief slot regions 180, whose presence or absence are indicative of the characteristics of the fiberoptic catheter, are placed radially about the handle region. Rotational alignment pin 190 is shown in a bore of handle 40.

Figure 7:
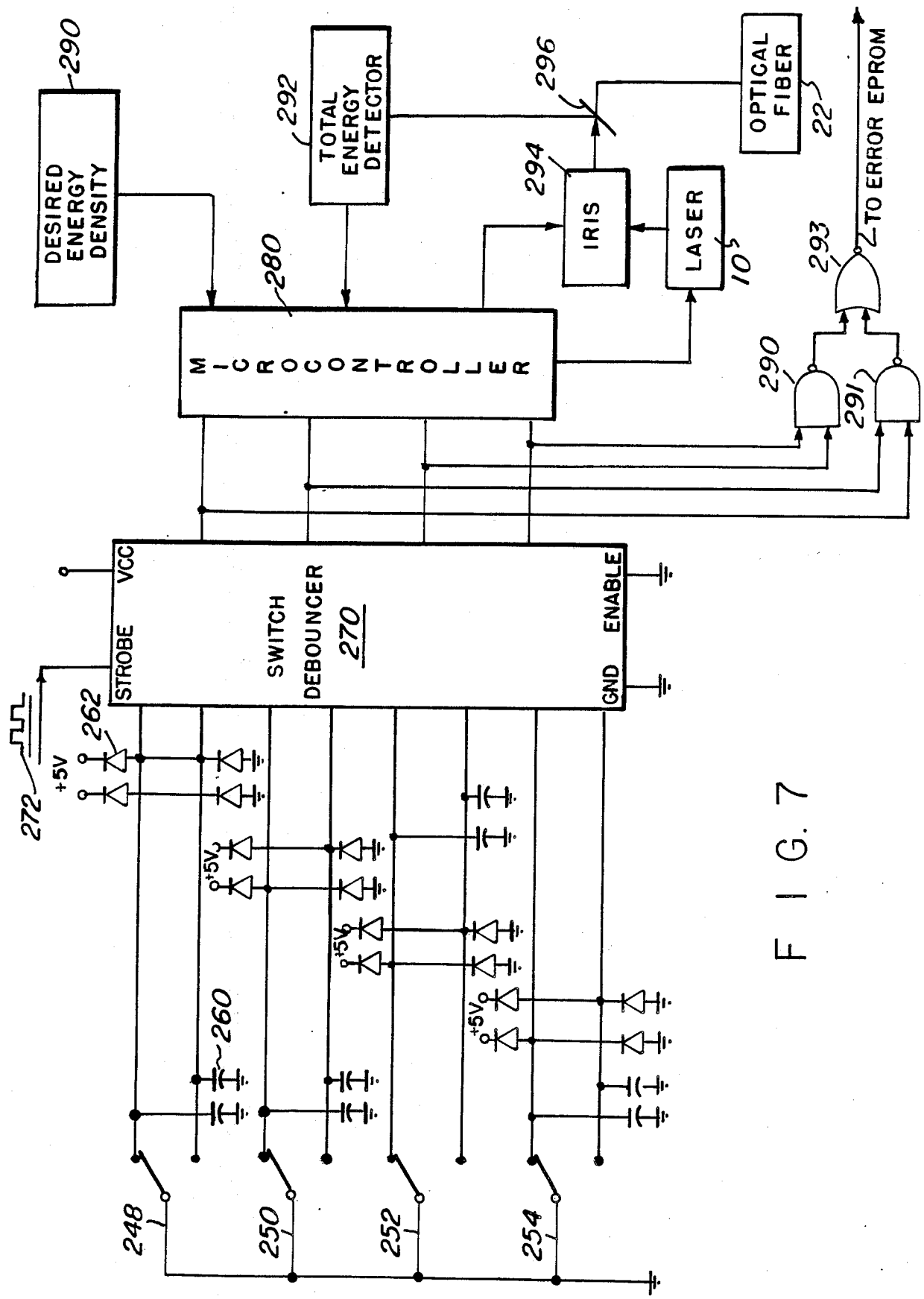
FIG. 7 is a schematic drawing of a microprocessor controlled circuit for use with the invention.

A circuit for decoding information about the fiberoptic catheter which employs a microprocessor is shown in FIG. 7. Switches 248, 250, 252 and 254, corresponding to the microswitches shown in FIG. 5, are activated by plungers 184. The switches are of a single pole double throw type and connect to a switch debouncer 270. Capacitors 260 and diodes 262 connect the switching lines to ground or the supply voltage as shown in FIG. 7. The capacitors and diodes filter high frequency signals and high voltage spikes that might be picked up by the switch lead wires.

When none of the switches 248–254 are activated, the outputs of the switch debouncer 270 will be high. All high signals to the input of microprocessor controller 280 indicates that there is no fiberoptic catheter in the fiberoptic coupler. When a fiberoptic catheter is present, a combination of high and low signals will indicate the diameter or other characteristic of the catheter. A total of fifteen different combinations can be decoded from a four switch input circuit.

A synchronizer clock signal 272 can be used as a strobe for the switcher debouncer 270. This will ensure that all inputs from switches 248–254 are stable when the microcontroller 280 reads its inputs.

NAND gates 290 and 291 and NOR gate 293 are used to generate via hardware a signal indicating that a catheter is not in place. This signal is used as an input signal to an EPROM which performs a hardware-software error check. A low voltage signal indicates a catheter is not in place and a high signal indicates that a fiber is in place.

Microprocessor 280 controls the laser power output to the fiberoptic catheter based on the information decoded from the fiberoptic coupler and selected energy density. Microprocessor 280 receives inputs from the fiberoptic coupler through the switch debouncer circuit 270, the doctor's desired energy density through input 290, and a total laser energy output from detector 292. A beam splitter 296 can be used to divert a portion of the laser beam to the detector 292. The microprocessor enables the pulsing of the laser 10 and adjusts a variable iris 294 to control the laser energy delivered to optical fiber catheter 22.

Figure 8:
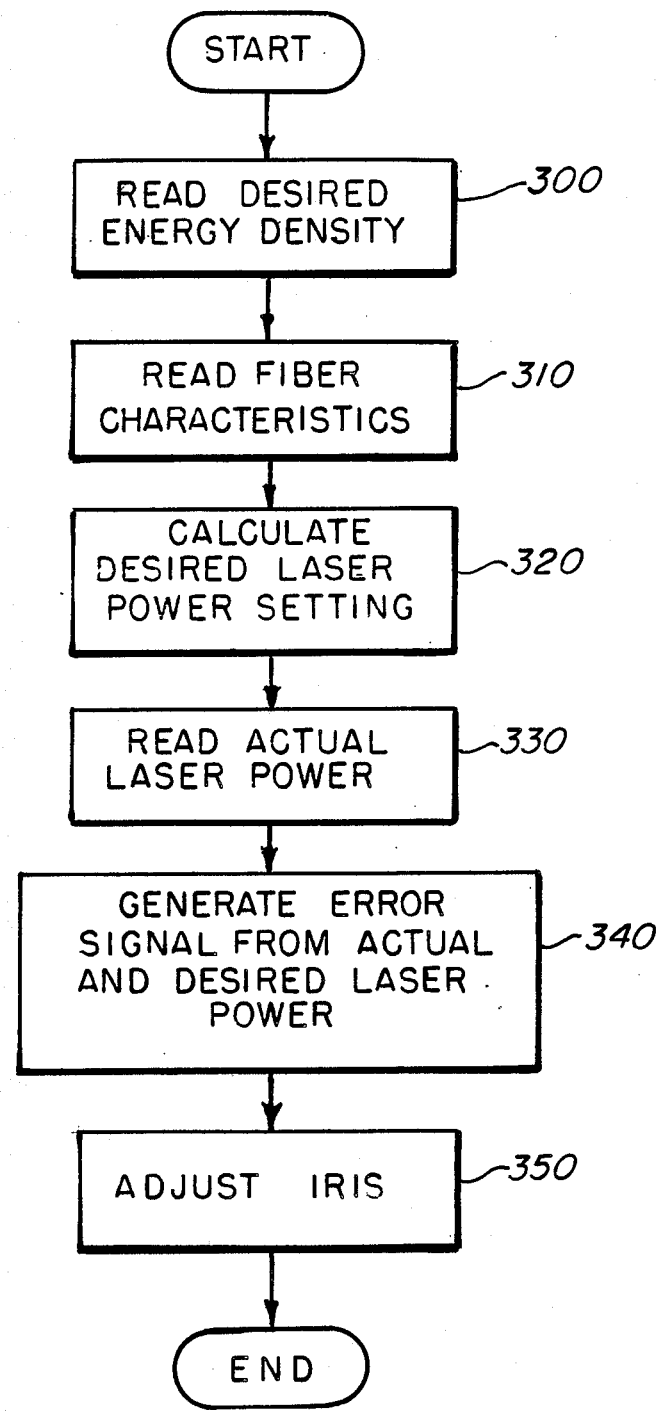
FIG. 8 is a flow chart of the microprocessor sequencing within the circuit of FIG. 7.

A flow chart for the microprocessor 280 is shown in FIG. 8. Upon initialization, the microprocessor reads the desired energy density step 300 which is selected by a doctor to achieve the desired ablation conditions for the fiberoptic catheter. Next, in step 310, the microprocessor reads the fiber characteristics presented to it from the optical coupler 20 through switch debounce 270. A calculation is made by the microprocessor in step 320 to determine the desired laser power settings to achieve the selected energy density in the specific optical fiber being used. A reading is made of the actual laser power in step 330. A comparison of the actual laser output power to the desired power level is made to produce an error signal in step 340. The error signal is used to adjust a variable iris 294 in step 350 so that the desired energy density is sent through optical fiber catheter 22.

Other encoding means such as magnetic or optical sensing schemes could be developed to work in conjunction with the design of the optical coupler of the present invention.

The present invention provides a fiberoptic coupler which accurately aligns an optical fiber to a laser light source and is able to detect the presence or absence of a fiber as well as to determine sufficient information as to fiber size to identify the diameter of the fiber being used.

While the invention has been described in connection with what is presently considered to be the preferred embodiment, it is to be understood that the invention is not limited to the disclosed embodiment, but can be intended to cover its modifications and equivalent arrangements within the spirit and scope of the appended claims.

What is claimed is:

1. A fiberoptic coupler for connecting an optical fiber to a laser light source comprising:
    a first connector portion adapted to be coupled to an end of an optical fiber;
    means, coupled to said first connector portion, for providing information indicative of the optical fiber;
    a second connector portion removably connected to said first connector portion; and
    means, coupled to said second connector portion, for decoding the information indicated by said providing means.

2. The fiberoptic coupler of claim 1 wherein:
    said first connector portion includes a male plug adapted to be coupled to an end of an optical fiber and having a locating pin, said providing means being located along said locating pin; and
    said second connector portion includes a female receptacle removably connected to said male plug and receiving said locating pin, said decoding means decoding the information located along said locating pin.

3. A fiberoptic coupler for connecting an optical fiber to a laser light source comprising:
    a male plug adapted to be coupled to an end of an optical fiber, the male plug having a locating pin;
    a providing means including grooves disposed on said locating pin indicative of information about said optical fiber;
    a female receptacle removeably connected to said male plug and receiving said locating pin;
    a decoding means coupled to said female receptacle including switches having controllable conductive states; and
    said grooves being selectively positioned relative to said switches to control the conductive state of said switches to provide information about said optical fiber.

4. The fiberoptic coupler of claim 3 wherein said grooves provide information about the diameter of said optical fiber.

5. The fiberoptic coupler of claim 1 wherein:
    said first connector portion includes a male plug adapted to be coupled to an end of an optical fiber and having an enlarged handle region, said providing means being located within said handle region; and
    said second connector portion includes a female receptacle removably connected to said male plug and mating said handle region, said decoding means decoding the information located within said handle region.

6. The fiberoptic coupler of claim 5 wherein:
    said providing means includes relief openings disposed in said enlarged handle region indicative of information about said optical fiber;

said decoding means including spring loaded plungers activating switches having controllable conductive states; and said relief slots being selectively positioned relative to said plunger to activate said switches to control the conductive state of said switches to provide information about said optical fiber.

7. The fiberoptic coupler of claim 6 wherein said relief openings provide information about the diameter of said catheter.

8. A fiberoptic coupler for connecting a fiberoptic catheter to a laser light source comprising:

a male plug portion, the male plug having a locating pin adapted to be coupled to an end of an optical fiber catheter, the locating pin having a plurality of grooves located at selected ones of a plurality of positions along said locating pin, said grooves being indicative of information concerning the catheter;

a female receptacle portion removably connected to said male plug portion; and means, disposed in said female receptacle portion, for sensing the location of said grooves in the male plug locating pin, the groove location indicative of the diameter of the optical fiber being coupled to the laser light source.

9. A fiberoptic coupler for connecting a fiberoptic catheter to a laser light source comprising:

a male plug portion, the male plug having a locating pin adapted to be coupled to an end of an optical fiber catheter, the locating pin having a plurality of grooves located at selected ones of a plurality of positions along said locating pin, said groove positions indicative of the diameter of the optical fiber catheter;

a female receptacle portion removably connected to said male plug portion; and sensing means including microswitches located at predetermined positions in said female receptacle portion, said receptacle portion positions corresponding to said plurality of positions along said locating pin, said microswitches sensing at which of said positions along said locating pin, grooves are provided.

10. A fiberoptic coupler for connecting a fiberoptic catheter to a laser light source comprising:

a male plug portion, the male plug having an enlarged handle region for supporting an end of an optical fiber catheter, the handle region having a plurality of relief openings located at selected ones of a plurality of positions within said handle region, said openings being indicative of information concerning the catheter;

a female receptacle portion removably connected to said male plug portion; and means, disposed in said female receptacle portion, for sensing the location of said openings in the male plug handle region, the opening location indicative of the diameter of the optical fiber being coupled to the laser light source.

11. A fiberoptic coupler for connecting a fiber optic catheter to a laser light source comprising:

a male plug portion, the male plug having an enlarged handle region for supporting an end of an optical fiber catheter, the handle region having a plurality of relief openings located at selected ones of a plurality of positions within said handle region, said openings being indicative of the diameter of the optical fiber being coupled to the laser light source;

a female receptacle portion removably connected to said male plug portion; and sensing means, disposed in said female receptacle portion, for sensing the location of said openings in the male plug handle region, said sensing means including microswitches located at predetermined positions in said receptacle portion, said receptacle portion positions corresponding to said plurality of positions within said handle region, said microswitches sensing which of said position in said handle region openings, are provided.

* * * * *